US008975584B2

(12) United States Patent
Sartorius et al.

(10) Patent No.: US 8,975,584 B2
(45) Date of Patent: Mar. 10, 2015

(54) IMPROVED-EFFICIENCY FIBRE-COUPLED TERAHERTZ SYSTEM (75) Inventors: Bernd Sartorius, Berlin (DE); Helmut Roehle, Berlin (DE); Dennis Stanze, Berlin (DE); Roman Dietz, Berlin (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 125 days.

(21) Appl. No.: 13/881,085

(22) PCT Filed: Oct. 25, 2011

(86) PCT No.: PCT/EP2011/005530
§ 371 (c)(1),
(2), (4) Date: Jul. 9, 2013

(87) PCT Pub. No.: WO2012/055574
PCT Pub. Date: May 3, 2012

(65) Prior Publication Data
US 2013/0306869 A1    Nov. 21, 2013

(30) Foreign Application Priority Data
Oct. 25, 2010    (DE) .................... 10 2010 049 658

(51) Int. Cl.
*G01J 5/22*    (2006.01)
*G01N 21/3581*    (2014.01)

(52) U.S. Cl.
CPC ............... *G01J 5/22* (2013.01); *G01N 21/3581* (2013.01)
USPC ........................................................ 250/338.4

(58) Field of Classification Search
CPC ........... G01N 21/3581; G01J 5/02; G01J 5/22
USPC ....................................................... 250/338.4
See application file for complete search history.

(56) References Cited

U.S. PATENT DOCUMENTS 7,291,839 B1 *    11/2007    Demers et al. ............. 250/341.1
2006/0152412 A1 *    7/2006    Evans et al. ............. 343/700 MS
(Continued)

FOREIGN PATENT DOCUMENTS

DE    102006010301 B3    6/2007
DE    102006010297 B3    7/2007
(Continued)

OTHER PUBLICATIONS

"International Application No. PCT/EP2011/005530, International Preliminary Report on Patentability mailed Jan. 24, 2013", 13 pgs.
(Continued)

*Primary Examiner* — Marcus Taningco
(74) *Attorney, Agent, or Firm* — Schwegman Lundberg & Woessner, P.A.

(57)    ABSTRACT

A terahertz system can be configured for producing and coherently detecting terahertz radiation. The system can comprise a laser light source and two THz antennas, a first of which is used as a transmission antenna and a second of which is used as a receiver antenna, which are each optically coupled to the laser light source by an optical fiber and can be activated by light from this laser light source, wherein the THz antennas each have a semiconductor chip to which antenna conductors have been contact-connected and which comprises at least one photosensitive active layer with a band edge wavelength which is longer than a wavelength of the laser light source and at least one layer, adjoining the active layer, with a band edge wavelength which is shorter than the wavelength of the laser light source, wherein the band edge wavelength of the active layer of at least one of the THz antennas is at least 200 nm longer than the wavelength of the laser light source.

11 Claims, 6 Drawing Sheets

(56) References Cited

U.S. PATENT DOCUMENTS

| | | | |
|---|---|---|---|
| 2008/0279227 A1 | 11/2008 | Nakayama et al. | |
| 2009/0296197 A1* | 12/2009 | Holzwarth et al. | 359/328 |
| 2010/0067918 A1* | 3/2010 | Federici et al. | 398/158 |
| 2010/0080505 A1* | 4/2010 | Sartorius et al. | 385/14 |
| 2011/0031400 A1 | 2/2011 | Sartorius et al. | |
| 2012/0129294 A1 | 5/2012 | Sartorius et al. | |

FOREIGN PATENT DOCUMENTS

| | | |
|---|---|---|
| DE | 102007012475 A1 | 9/2008 |
| DE | 102007044839 A1 | 5/2009 |
| FR | 2870386 A1 | 11/2005 |

OTHER PUBLICATIONS

"International Application No. PCT/EP2011/005530, International Search Report and Written Opinion mailed Mar. 2, 2012", 17 pgs.

Dyson, A., et al., "Comparison of Type I and Type II Heterojunction Unitravelling Carrier Photodiodes for Terahertz Generation", IEEE Journal of Selected Topics in Quantum Electronics, 14(2), (2008), 277-283.

Francoeur, S., et al., "Band gap of $GaAs_{1-x}Bi_x$, $0<x<3.6\%$", Applied Physics Letters, 82(22), (2003), 1581983 (3 pgs.).

Pacebutas, V., et al., "Characterization of low-temperature molecular-beam-epitaxy grown GaBiAs layers", Semiconductor Science and Technology, 22(7), (2007), 819-823.

Pacebutas, V., et al., "Terahertz time-domain-spectroscopy system based on femtosecond Yb:fiber laser and GaBiAs photoconducting components", Applied Physics Letters, 97(3), (2010), 031111 (3 pgs.).

Stanze, D., et al., "Coherent CW terahertz systems employing photodiode emitters", 34th International Conference on Infrared, Millimeter, and Terahertz Waves, 2009. IRMMW-THz 2009., (2009), 1-3.

"International Application No. PCT/EP2011/005530, English Translation of International Preliminary Report on Patentability mailed Jan. 24, 2013", (Apr. 25, 2013), 11 pgs.

"$Ga_x In_{1-x}$ As: Band structure and carrier concentration", [online]. [archived on Oct. 24, 2007]. Retrieved from the Internet: <URL: http://web.archive.org/web/20071024121629/http://www.ioffe.rssi.ru/SVA/NSM/Semicond/GaInAs/bandstr.html>, (Oct. 24, 2007), 5 pgs.

* cited by examiner

IMPROVED-EFFICIENCY FIBRE-COUPLED TERAHERTZ SYSTEM

PRIORITY CLAIM TO RELATED APPLICATIONS

This application is a national stage application under 35 U.S.C. §371 of PCT/EP2011/005530, filed Oct. 25, 2011, and published as WO 2012/055574 A1 on May 3, 2012, which claims priority to German Application No. 10 2010 049 658.8, filed Oct. 25, 2010, which applications and publication are incorporated by reference as if reproduced herein and made a part hereof in their entirety, and the benefit of priority of each of which is claimed herein.

The invention relates to a terahertz system for producing and coherently detecting terahertz radiation, according to the preamble of the main claims.

Thereby, electromagnetic radiation of a frequency between 0.05 THz and 20 THz is indicated as being terahertz radiation, wherein the frequency is typically between 0.1 THz and 10 THz. These frequencies are very high for an electronics signal processing, but on the other hand are very low compared to the frequencies typical for photonics, so that quantum energy of terahertz radiation is still very small. Measurement systems operating with terahertz radiation are therefore very difficult to realise, which is why terahertz radiation forms the last region of the electromagnetic spectrum which has not yet been exploited to a satisfactory extent for practical applications.

Terahertz systems of the type described here utilise optoelectronic semiconductor chips for producing and detecting terahertz radiation. A terahertz system of the type according to the preamble thereby comprises a laser light source and two THz antennae which in each case are optically coupled to the laser light source via a fibre-optic, can be activated by light of this laser light source, and of which one serves as a transmitter antenna and a second as a receiver antenna. Thereby, the terahertz antennae each comprise a semiconductor chip which is contacted by the antenna conductors and which comprises at least one photo-sensitive active layer with a band edge wavelength larger than a wavelength of the laser light source, as well as at least one layer which is adjacent the active layer and which has a band width wavelength smaller than the wavelength of the laser light source. The antenna conductors are thereby typically integrated on the respective semiconductor chip. The laser light source can thereby be designed for producing shorter pulses or for producing beat signals in the THz region by way of superimposing two laser waves of slightly different wavelengths. The wavelength of one laser light source in the present document is defined in each case as the centre of gravity of a wavelength spectrum of the light produced by the light source. Terahertz radiation can now be produced with such terahertz systems and be coherently detected by way of applying a voltage to the antenna conductor of the transmitter antenna, whilst the transmitter antenna and the receiver antenna are simultaneously activated with coherent radiation of the laser light source and a current produced in the receiver antenna is measured by way of a sensor connected to the antenna conductors of the receiver antenna. In this manner, a received signal for different delays of a time-of-flight between the laser light source and the receiver antenna or the transmitter antenna can be detected, in order to examine a sample arranged between the transmitter antenna and the receiver antenna.

Terahertz systems of this type are known e.g. from the document DE 10 2007 044 839 A1. These terahertz systems can be advantageously realised in a compact, robust and flexible manner by way of the use of fibre-optics for the connection of the laser light source to the THz antennae. The terahertz systems of this type and which are known from the state of the art however still have unsatisfactory powers, wherein the relatively low transmitting powers of the transmitter antennae as well as limited sensitivities of the receiver antennae render necessary long integration times on measuring, which leads to disadvantageously slow measurements. Also, strongly absorbing materials can no longer be beamed through and small signals cannot be reliably detected, even with relatively low material thicknesses.

It is therefore the object of the present invention to suggest a comparable, but efficiency-improved terahertz system, with which, with a given power of the laser light source, one can realises a greater transmitting power and an improved receiving sensitivity, wherein the terahertz system should be comparably compact and robust.

According to the invention, this object is achieved by a terahertz system with the characterising features of the main claim in combination with the features of the preamble of the main claim. Advantageous developments and designs of the invention are to be deduced from the features of the dependent claims.

The invention thus envisages the band edge wavelength of the active layer of at least one of the THz antennae being at least 200 nm larger than the wavelength of the laser light source. Preferably, this is the case for the transmitter antenna as well as for the receiver antenna, wherein however both can be constructed differently and do not need to have identical band edge wavelengths. One succeeds in the active layer having a very high absorption coefficient for the light of the laser light source, due to the comparatively large distance between the band edge wavelength of the active layer and the wavelength of the laser light source. This entails the advantage that the light of the laser light source which serves for activating the terahertz antenna is greatly absorbed there, even with a thin design of the active layer.

If precisely electron-hole pair is produced per absorbed photon, and the beamed-in optical power is kept constant, then with short-waved light with high photon energy, less freely movable charge carriers are produced than with the use of longer waved, but still absorbed light with smaller photon energy. Short-waved light per se is therefore unfavourable for a photoeffect which is to be effective as possible with respect to the beamed-in power. Moreover, the excess energy of the high-energetic photons is moreover yet converted into heat, which typically compromises the functioning of semiconductor components. The photo effect is now however only a part step in the production and detection of terahertz radiation. If, with the conversion of the photoeffect in terahertz radiation, the high-frequency characteristics give the impression of very thin, absorbing layers being particularly advantageous, then a new total assessment can result. Then, in any case, the demand of a high light absorption in very thin layers arises. This can be achieved by the short-waved light which is demanded here. As a whole therefore, in the case of the transmitter antenna, a large THz transmitting power and in the case of the receiver antenna, a very high THz sensitivity can be achieved, since the high-frequency characteristics can be optimised by very thin, active layers, and a good light absorption is achieved by way of the wavelength of the light source being at least 200 nm larger than the band edge wavelength. Thus one can circumvent the problem of the THz antennae being either not quick enough due to too thick active layers or not having a high power or being sensitive enough due to too low a light absorption.

The described advantage is particularly pronounced if the band edge wavelength of the active layer at least of one of the THz antennae is at least 250 nm larger than the wavelength of the laser light source. This is due to the fact that the absorption coefficient of the active layer formed from a photo-sensitive material at least firstly rises very steeply from the band edge wavelength towards smaller wavelengths. It is advantageous if the band edge wavelength of the active layer is at least 300 nm shorter than the band edge wavelength of the adjacent layer, in order to render possible such a large distance between the band edge wavelength of the active layer and the wavelength of the laser light source.

Here, in each case a wavelength $\lambda$ which is related to a band gap $\Delta E$, thus to a distance between the valence band and a conduction band, according to $\lambda = hc/\Delta E$ is indicated as a band edge wavelength, wherein h is the Planck constant and c the speed of light. The band gap can thereby also be dependent on the layer thickness of the respective layer. Inasmuch as the band gap and thus also the band edge wavelength are temperature-dependent, here it is always their values at operating temperature, typically at between 10° C. and 40° C., preferably at 20° C. and which are defined in the usual manner which are meant.

By way of not too small a distance between the wavelength of the laser light source and the band edge wavelength of the at least one layer adjacent the active layer, it is ensured that the light of the layer light source is not absorbed in the adjacent layer, which would drastically worsen the efficiency of the THz antenna and lead to a disadvantageous additional development of heat.

Even if the particular characteristics which are mentioned here under certain circumstances could also only apply to the transmitter antenna or only to the receiver antenna, it is of course particularly advantageous if this is the case for both THz antennae. With useful embodiments moreover, a preferably controllable, optical delay circuit is connected between the laser light source and one of the THz antennae, so that a time-slot of optical control signals for activating the two THz antennae can be shifted relative to one another. By way of this, a damping of the terahertz radiation as well as a delay of a time-of-flight of this can be precisely determined by a sample arranged between the transmitter antennae and the receiver antennae.

It is advantage if the band edge wavelength of a semiconductor material which is forms the active layer and which belongs to at least one of the THz antennae is at least 1600 nm, so that the mentioned conditions can be kept to. The active layer thereby on account of the quantum well effect, can itself also have a lower band edge wavelength which however at all events still has an adequately large distance to the wavelength of the laser light. The active layer for this can e.g. be formed from InGaAs which has a band edge wavelength of about 1650 nm or preferably chiefly contain InGaAs. Thus the active layer can be formed e.g. from InGaAs doped with beryllium, thus from InGaAs:Be. A substrate of the semiconductor chip of the THz antenna can thereby be formed from InP. The active layer and the at least one layer which is adjacent thereto can e.g. be grown epitactically onto this substrate.

One can envisage the active layer of at least one of the THz antennae having a thickness which at the most corresponds to a penetration depth of the light of the laser light source, in order to achieve a rapid responsiveness which is important for the production or detection of terahertz radiation. The penetration depth is thereby defined as a depth at which a beam intensity of the incident light of the laser light source has reduced to a share of 1/e of the magnitude of the beaming intensity on a surface irradiated with the light.

Typically, at least the receiver antenna of the THz system will be based on a photoconductor. The same can also be the case with regard to the transmitter antennae. The semiconductor chip of a photoconductor-based THz antenna can comprise one or also several active layers. As a rule thereby, the active layer or each of the active layers is embedded in each case between two adjacent layers. The adjacent layers thereby serve as recombination layers. It is particularly advantageous if the semiconductor chip has a periodic layer structure with a multitude of alternately arranged active layers and recombination layers, wherein e.g. 100 or more active layers can be provided. By way of this, on the one hand it is possible to design the active layers very thinly, in order to realise an adequately rapid photoconductor, but at the same time to achieve a high photocurrent with incident light of the laser light source, said high photocurrent being compelling for an efficient terahertz system. For this, the active layers of the THz antennae based on a photoconductor should not be thicker than 12 nm, preferably 10 nm or thinner, wherein particularly good results are achieved if the active layers are each not thicker than 8 nm, even better 6 nm thick at the most. The recombination layers can e.g. be designed with a thickness of at the most 10 nm, typically with a thickness of about 8 nm. A layer structure which is formed by the active layers and the recombination layers can therefore be contacted with the antennae conductors at a surface or at lateral end-faces.

InAlAs which has an adequately short band edge wavelength lends itself as a material for the at least one layer which is adjacent the active layer, with a photoconductor. The at least one layer serving as a recombination layer can thus preferably chiefly contain InAlAs and e.g. be formed from InAlAs provided with electrons traps or recombination centres.

The transmitter antenna can also be based on a photodiode instead of a photoconductor. The active layer which is preferably formed at least chiefly of InGaAs then as a rule is 400 nm thick at the most, preferably not thicker than 300 nm. With embodiments which are particularly advantageous with regard to a rapid responsiveness of the photodiode, the active layer of the photodiode is thereby not thicker than 200 nm or 100 nm. The at least one layer which is adjacent the active layer and which here can be indicated as a contact layer, can contain e.g. InGaAsP or InGaAlAs and preferably be chiefly formed from one of these materials. Typically thereby, again two adjacent layers are provided, between which the active layer is arranged, wherein here one of the adjacent layers is p-doped and one n-doped. The band edge wavelength of these quaternary layers can be set by way of the mixing ratio. The band edge wavelength of these layers must be smaller than that of the active layer, but the discontinuity in the conduction band and valence band cannot be too large, for a good functioning of the photodiodes. Typically, boundary layers with 1200 nm band edge wavelength represent a lower limit for an active layer of InGaAs on InP with a band edge wavelength of 1650 nm. These layers are well transparent for wavelengths above 1250 nm, which permits a desired large distance of the laser light wavelength to the band edge wavelength of the active layer, without absorption in the boundary layers. A particularly high efficiency of the transmitter antenna can be achieved by way of the use of a photodiode.

One can envisage the adjacent layer or at least one of the adjacent layers of at least one of the THz antennae serving at a waveguide, into which the light of the laser light source is coupled through the fibre-optic connecting this THz antennae to the laser light source, propagating in a plane defined by the layer. Thus an advantageously compact construction can be realised and achieved, so that the photon energies of the light of the laser light source can be absorbed very effectively in the active layer. A design of at least one of the adjacent layers as a waveguide, through which the light of the layer light source is fed in, particularly lends itself in the case of the transmitter antenna if this is photodiode-based.

The wavelength of the laser light source of the terahertz system can lie e.g. between 1260 nm and 1360 nm, in the so-called O-band of fibre telecommunication, preferably between 1260 nm and 1310 nm. Additionally to the desired distances to the band edge wavelengths of the active layer and of the at least one adjacent layer, there is further advantage of an almost negligible dispersion in the fibre-optics, for which e.g. SSMF standard single mode fibres can be used. This in turn has a particularly great advantage with the use of a pulsed layer, in order to avoid a pulse broadening which impedes the functioning of the THz antennae.

The use of a pulsed laser as a laser light source for activating the THz antennae is particularly advantageous if both THz antennae are based on photoconductors, since a high transmitting power and a high receiving sensitivity can be realised particularly well with a pulsed laser. One can use any femtosecond pulsed laser of a suitable wavelength for an embodiment of the terahertz system as a pulsed system.

With other embodiments, the laser light source can be given by a two-mode laser or a system of two lasers, and be configured for producing a beat signal of two laser waves, wherein a beat frequency of this beat signal should be at least 0.05 THz and typically lies between 0.05 and 20 THz, preferably between 0.1 THz and 10 THz, so that the terahertz radiation can be produced with a suitable frequency and wavelength. The embodiment with a two-mode laser or a system of two lasers and the activation of the THz antennae with a corresponding beat signal leads to particularly satisfactory results if the transmitter antenna is photodiode-based, since the problem of too low transmitting powers which is particularly serious with an activation by a beat signal can be avoided by way of the use of a photodiode-based transmitter antenna.

Embodiment examples of the invention are hereinafter explained by way of the FIGS. 1 to 13. There are shown in:

FIG. 1 a schematic representation of a terahertz system for the producing and coherently detecting terahertz radiation, FIG. 2 a plan view of a receiver antenna of the terahertz system of FIG. 1, FIG. 3 a cross section through a semiconductor chip of the receiver antennae of FIG. 2, FIG. 4 in a representation corresponding to FIG. 3, a cross section through a semiconductor chip of a receiver antennae, in a modification of the embodiment of the FIGS. 2 and 3, FIG. 5 a plan view of the transmitter antenna of the terahertz system of FIG. 1, FIG. 6 in a diagrammatic representation, a wavelength dependency of an absorption coefficient of an active layer of a terahertz antenna, FIG. 7 a diagram with a course of radiation intensity in dependence on a penetration depth into a photosensitive active layer of a relatively large thickness, FIG. 8 in a representation corresponding to FIG. 7, a course of the radiation intensity at the same wavelength, but with a significantly smaller thickness of the active layer, FIG. 9 in a representation corresponding to the FIGS. 7 and 8, a course of the radiation intensity with the active layer of a smaller thickness of FIG. 8, for light of a shorter wavelength, FIG. 10 in a representation corresponding to FIG. 1, a plan view of a terahertz system in another embodiment, FIG. 11 as cross section through a semiconductor chip of a transmitter antenna of this terahertz system, FIG. 12 a perspective representation of a photodiode in this transmitter antenna and FIG. 13 a perspective representation of the complete a transmitter antenna of the terahertz system of FIG. 10.

Figure 1:
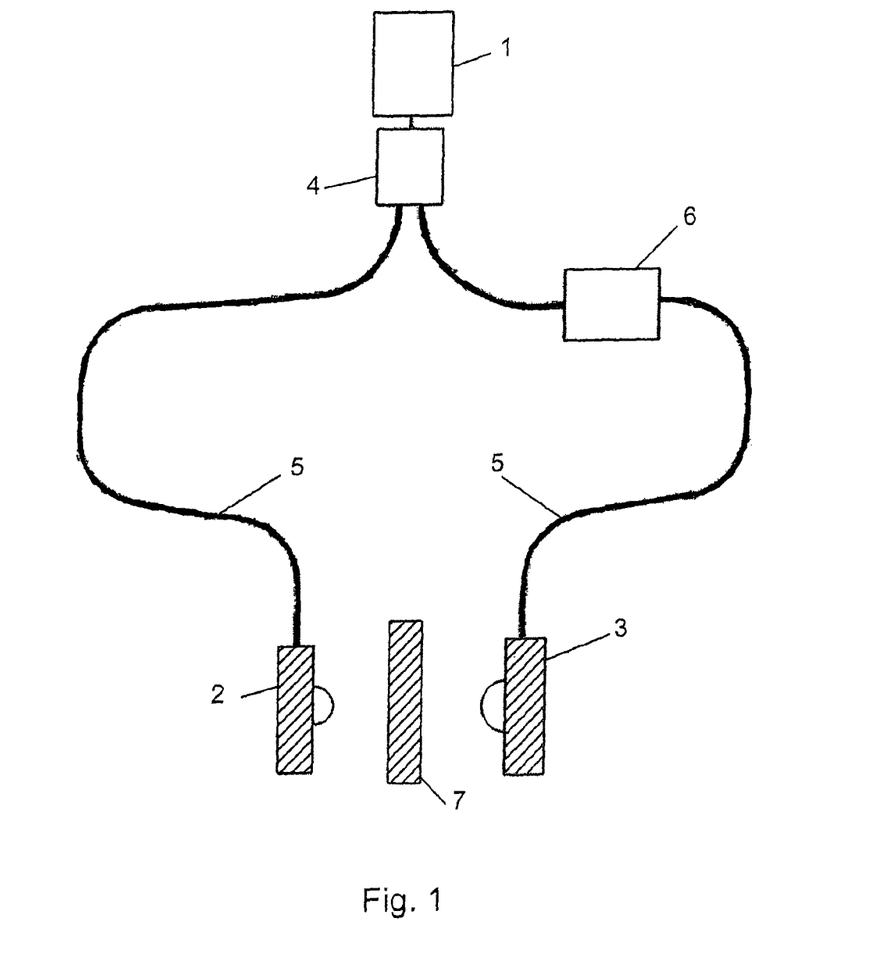

The terahertz system shown in FIG. 1 comprises a laser light source 1, a transmitter antenna 2 and a receiver antenna 3. With regard to the transmitter antenna 2 and the receiver antenna 3, it is each the case of a THz antenna activatable by light of the laser light source 1. For this, a beam splitter 4 is arranged behind an output of the laser light source 1, wherein the transmitter antenna 2 and the receiver antenna 3 are connected in each case by way of a fibre-optic 5 to one of two outputs of the beam splitter 4.

With regard to the laser light source 1, it is the case of a pulsed laser, wherein the centre of gravity of a mode comb of this pulsed later lies in the O-band. A wavelength of the laser light source 1 which is defined as a centre of gravity of the mode comb thereby lies at 1310 nm. With regard to the fibre optics 5 it is the case of SSMF lightguides, for example of the type SMF 28, which have a dispersion zero point at this wavelength. A controllable, optical delay circuit 6, with which a relative time-slot of optical control signals for activating both THz antennae can be shifted, is arranged at an input or in a course of one of the fibre optics 5. For this, the delay circuit 6 can e.g. comprise a delay conductor which can be subjected to a variable electric field. Finally, a sample 7 which can be examined with the terahertz system and which is arranged between the transmitter antenna 2 and the receiver antenna 3 is represented.

The pulsed laser forming the laser light source 1 can be a fibre pulsed laser, e.g. with praseodymium doping, or a semiconductor pulsed laser, e.g. based on an InGaAsP/InP material system. A dispersion compensation with gratings or with special fibres is unnecessary since the fibre optics 5 display no dispersion at the wavelength of the laser light source 1. A complicated adjustment of a dispersion compensation is thus done away with, wherein fibre lengths of the fibre optics 5 can be up to a few meters and can be changed in length, without any problem.

Figure 2:
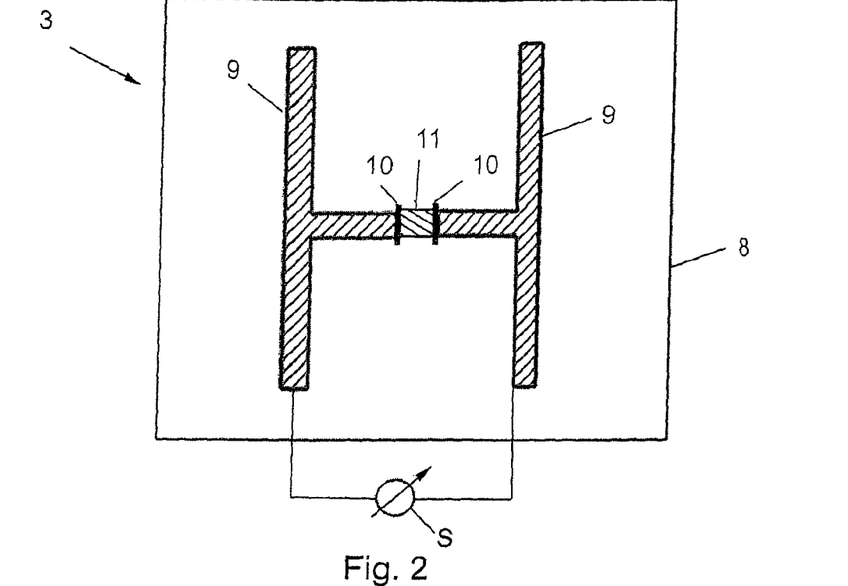

FIG. 2 shows the receiver antenna 3 of the terahertz system of FIG. 1. This receiver antenna 3 is based on a semiconductor chip with a substrate 8 of InP. This substrate 8 carries to antenna conductors 9 which are each connected via an electrical contact 10 to a light-sensitive region 11. The fibre optic 5 which connects the receiver antenna 3 to the laser light source 1 is led such that the laser light source 11 can illuminate the light-sensitive region 11 through the fibre-optic 5 from above. If the light of the layer light source 1 is incident there, the light-sensitive region 11 becomes electrically conductive. An electrical current is therefore induced between the waveguides 9, if the receiver antenna 3 is simultaneously subjected to an electrical field which is caused by an electromagnetic wave correlated temporally with the light of the laser light source 1. This current is measurable with a sensor S which is shown only schematically and which is connected to the antenna conductors 9. Thus a terahertz radiation which is produced with the transmitter antenna 2 activated by the laser light source 1 can be coherently detected with the receiver antenna 3.

Figure 3:
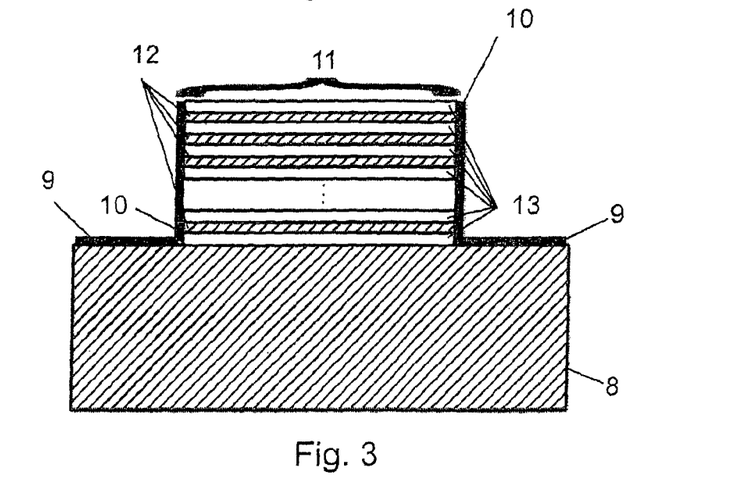

A detail of the receiver antenna 3 as a cross section is represented in FIG. 3, wherein this detail in particular includes the light-sensitive region 11. In this light-sensitive region 11, a photoconductor is arranged on a substrate 8 which comprise a multitude of between 20 and 100 active layers 12. These active layers 12 are formed from InGaAs which is doped with beryllium under certain circumstances and each have a layer thickness of 12 nm, 10 nm, 8 nm or also only 6 nm, depending on the embodiment. Each of the active layers 12 is embedded between two adjacent layers 13 which have a thickness in each case of about 8 nm and are formed from doped InAlAs which is provided with electron traps or recombination centres. The active layers 12 and the layers 13 which are adjacent thereto and which are grown epitactically onto the substrate 8, thus form a periodic layer structure above the substrate 8 of the semiconductor chip. A band edge wavelength of the adjacent layers 13 is roughly 900 nm and is thus significantly smaller than the wavelength of the laser light source 11. The adjacent layers 13 which alternate with the active layers 12 here serve as recombination layers which very quickly again capture charge carriers which are released due to the incidence of light, in the active layers 12 due to their small thickness.

Figure 4:
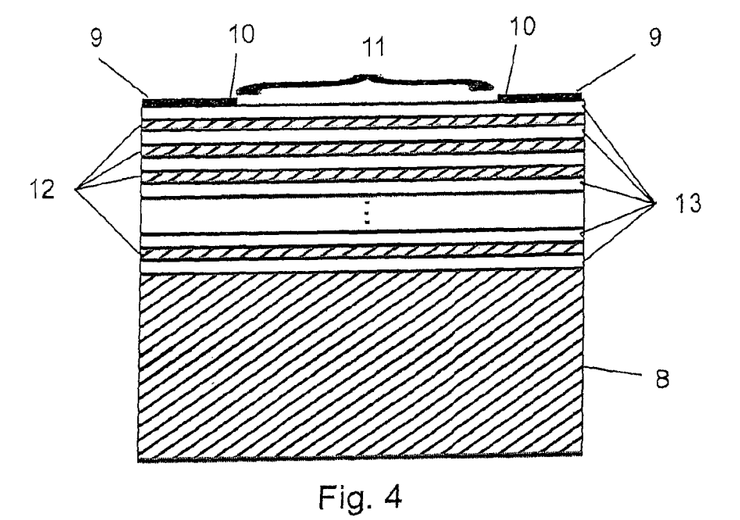

The thinner the active layers 12 the better is this decisive effect of the recombination layers on the charge carriers in the active layers 12. With thin layers however, the so-called quantum well effect occurs, which results in the effective band edge wavelength shifting to smaller wavelengths with increasingly thinner, embedded layers. Whereas thick InGaAs on an InP substrate has a band edge wavelength of 1650 nm, thicknesses of 12 nm for the layers 12 in FIG. 3 lead to an effective band edge wavelength of 1600 nm. Even thinner active layers of 10 nm, 8 nm or 6 nm thickness are advantageous for the optimisation of the function of the recombination layers. Thereby, the band edge wavelength however shifts further to about 1550 nm, 1500 nm and 1450 nm, wherein these band edge wavelengths can also be still increased somewhat by way of suitable mixing ratios of Ga and In the INGaAs. With this, absorption would no longer be effected with the laser sources with wavelengths of 1550 nm and which are applied in conventional terahertz systems for comparable THz antenna for excitation. For the layer with 12 nm thickness used until now and with a band edge at 1600 nm however, the light absorption is already present with wavelengths of 1550 nm, wherein the excess photon energy converted into heat is then very small. This therefore represents a very favourable wavelength correlation according to conventional observation. However, the absorption in an individual layer which is only 12 nm thin is so small that an adequate photoeffect is only achieved with a periodic repetition of the structure. What has been realised are e.g. 100 periods, which leads to a summed thickness of the absorbing layers of 1.2 μm. This thickness corresponds to the penetration depth of the light at this wavelength. The creation of the layer package is effected in a demanding and time-consuming epitaxy process in an expensive molecular beam epitaxy installation. The manufacture is simpler and less expensive if the function is achieved with fewer layers. This is possible if the laser wavelengths, as suggested here, is displaced to the short-waved region and thus as demanded, a wavelength difference of at least 200 nm, even better at least 250 nm is set for the effected band edge wavelength of the absorbing material. The penetration depth of the light is then significantly lower and since a summed thickness larger than this penetration depth brings no improvement, the number of periods can now be significantly reduced to e.g. only 20 active layers 12. With a smaller period number and a smaller thickness of the total package, a complicated mesa-structuring and side contacting as in Picture 3 is no longer necessary and one can use simpler planar structures with contacts lying at the top, as in Picture 4. Particularly advantageous wavelengths with the use of fibre connections between laser light source 1 and THz antennae lie in the region around 1310 nm, the so-called O-band of the telecommunication. There, the fibres specifically have a zero dispersion, so that the difficult dispersion compensation which is otherwise necessary in particular with the transmission of short pulses is done away with. The wavelength distance at 290 nm is very large with the use of a wavelength of 1310 nm and an active layer thickness of 12 nm with an effective band edge wavelength at 1600 nm. This means that the advantages of the very good and simple transmission of the pulses via the fibres can be combined with the advantages of antennae with a very low period number. The advantageous laser wavelength around 1310 nm—of course also yet slightly smaller wavelengths from the O-band can be used—opens up a scope for play, in order to optimise the effect of the recombination layers by way of even thinner active layers 12. The distance of the laser wavelength to the effective and edge wavelength with a suitably selected mixing ration of the InGaAs forming the active layers 12, is still about 250 nm or 200 nm and is thus still advantageously large for a good light absorption, even with layers with 10 nm, 8 nm thickness. This distance under certain circumstances can even be realised with layer thicknesses of only 6 nm. The advantageous laser wavelength of 1310 nm can thus also be combined with optimised, thin layers with a large wavelength difference to the effective band edge of the active layer 12, as was previously the case.

In each case, only a few of the layers 12 and 13 are represented in FIG. 3, whereas an inner-lying larger part of these layers 12 and 13 has been left out. What can be well recognised in FIG. 3 are the electrical contacts 10 which are connected to the antenna conductors 9 and contact the photoconductor here laterally and the end-faces FIG. 4 shows a cross section through a part of a similar THz antenna which corresponds to the detail of FIG. 3, and this antenna can be used instead of the receiver antenna 3 of the FIGS. 2 and 3 and differs from this only by way of a different contacting of the photoconductor. Recurring features are thereby again provided with the same reference numerals. The layers 12 and 13 forming the photoconductor here may also be larger surfaced and under certain circumstances can be deposited onto the substrate 8 over the whole surface. Differing from the design shown in FIG. 3, here the photoconductor is not contacted at the end-faces, but on a surface of the uppermost layer 13.

Figure 5:
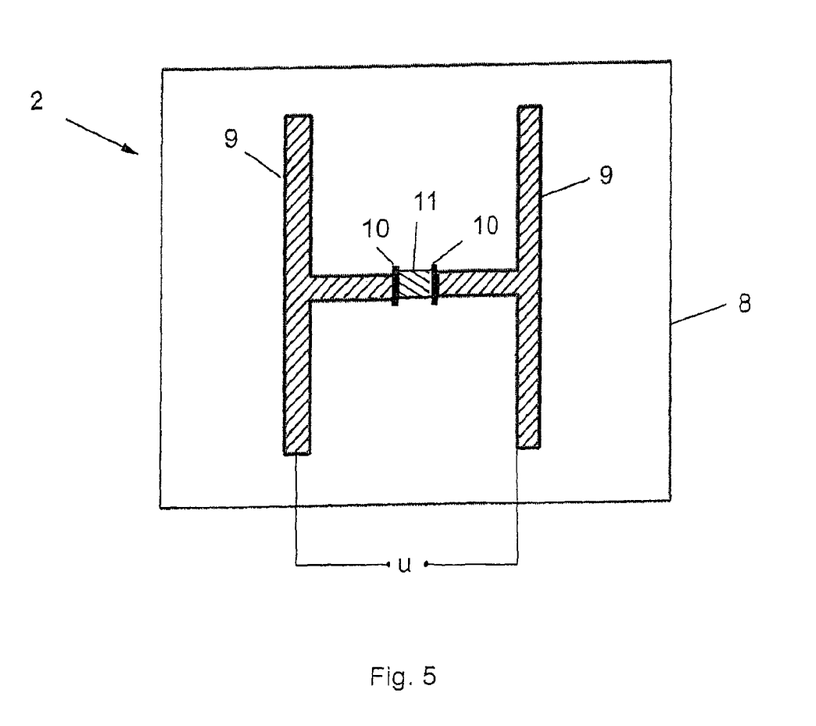

The transmitter antenna 2 is represented in FIG. 5 and differs from the receiver antenna 3 only by way of the fact that the antenna conductor 9 instead of the sensor S is connected to a voltage source which is shown only very schematically. Features which correspond to the already describe features of the receiver antenna 3 are again provided with the same reference numerals. A short current pulse flows between the antenna conductors 9 as soon as a light pulse from the laser light source 1 hits the light-sensitive region 11 of the transmitter antenna 2, due to the fact that here a voltage U is present at the antenna conductors 9, and this in turn leads to the transmitter antenna 2 emitting an electromagnetic wave, which corresponding to a pulse length of the light pulses which lie in the femtosecond region (typically in the region of a few 100 fs and below), has a frequency lying in the terahertz region and can be coherently detected with the previously described receiver antenna 3.

Figure 6:
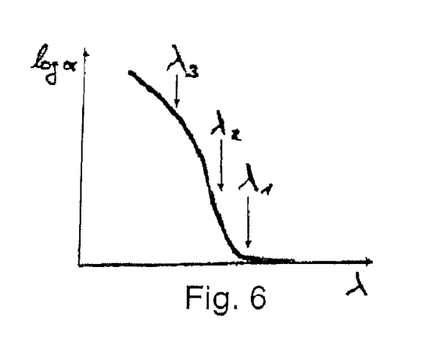

In a logarithmic representation, FIG. 6 shows a dependency of an absorption coefficient α of the active layer 12 on a wavelength λ of incident light. What is easily recognised is that a course of the absorption coefficient α at the band edge wavelength of the active layer 12 which is indicated here at $\lambda_1$ displays a break. The active layers 12 are transparent for larger wavelengths λ, since photon energy of corresponding light is not sufficient, in order to lift an electron out of a valence band into a conduction band. However, departing from the band edge wavelength, a steep rise of the absorption coefficient α is to be recognised towards smaller wavelengths λ. With conventional terahertz systems, light sources with wavelengths which are only slightly smaller than the band edge wavelength of a photo-sensitive material of the THz antennae are used for activating the THz antennae and specifically in a very deliberate manner, in order to prevent a development of heat in the photosensitive material as much as possible. This is based on the recognition that an energy excess which is given by a difference between photon energy of the light used for activation and a band distance between the valence band and the conduction band, is converted into heat. An excitation wavelength which is typical for conventional terahertz systems is indicated in FIG. 6 as $\lambda_2$. The absorption coefficient α is still relatively small for light of this wavelength.

Figure 7:
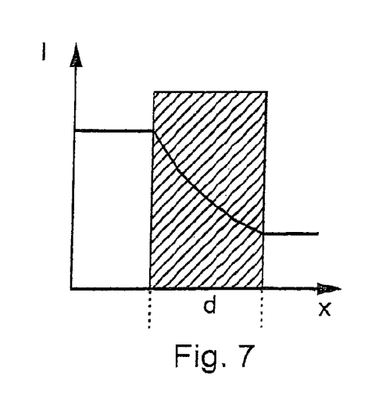

It is shown in FIG. 7 how light of the wavelength $\lambda_2$ is absorbed in a layer which consists of the same material as the active layers 12, but thereby has a relatively large thickness d. Thereby, the radiation intensity I is shown in dependence on a location coordinate x, wherein an x-axis of the respective coordinate system stands perpendicularly on the mentioned layer. A large part of the light is absorbed in the layer due to the relatively large thickness d, despite the absorption coefficient α which is small for this wavelength $\lambda_2$. The conditions represented in FIG. 7 correspond to those with the use of combinational photoconductors for realising a THz antenna. Thereby, the efficiency of the photoeffect is optimised, since the photon energy here is only just sufficient for triggering a photoeffect.

Figure 8:
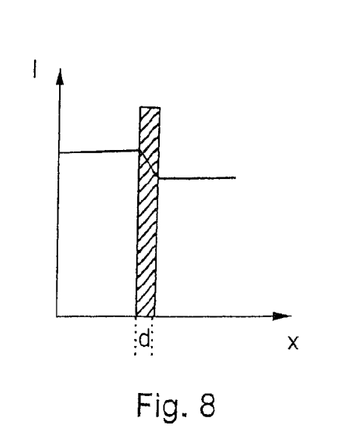

FIG. 8 in a representation corresponding to FIG. 7 shows the course of the radiation intensity I with a smaller layer thickness d which is to be strived for, in order to render the photoconductor adequately quick for an efficient production or detection of terahertz radiation with THz antennae of the described type. As is deduced from the course of the radiation intensity I in FIG. 8, the light with the wavelength $\lambda_2$ lying close to the band edge wavelength is now only yet absorbed to a very low share, which is why only a correspondingly low number of charge carriers is lifted into the conduction band. Despite the photoeffect which is in principle very effective in the energy balance at this wavelength $\lambda_2$, only very few photo charge carriers are produced on account of the very thin layers, and thus only very low efficiency of the respective THz antenna based on an opto-electronic semiconductor chip results.

Figure 9:
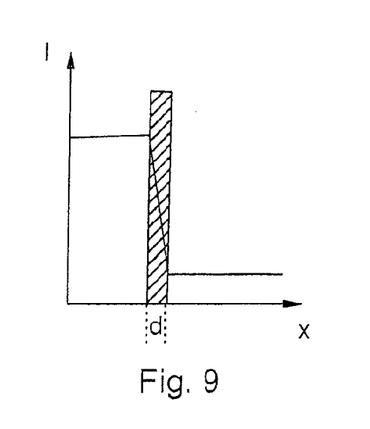

FIG. 9 finally in a representation corresponding to FIGS. 7 and 8 shows the course of a radiation intensity I with the same small layer thickness d as in FIG. 8 for the case that light of the laser light source 1 with a significantly smaller wavelength is used, which is indicated at $\lambda_3$ in FIG. 6. Despite the small layer thickness d, a very large share of the light is absorbed and accordingly a relatively large number of charge carriers is lifted into the conduction band due to the larger absorption coefficient α. This illustrates why the THz antennae of the terahertz system of FIG. 1 by way of the activation with the laser light source 1 operate in a very efficient manner, even if the photoeffect here is less efficient with regard to the energy balance, since it is accompanied by a greater production of heat.

The starting point of the solution suggested here is thus to depart from the use of femtosecond lasers, whose wavelengths lie only slightly above the band edge wavelength of the applied photosensitive materials and not to necessarily design the photosensitive layers of the terahertz antennae with such a band edge, that the laser wavelengths can just about be absorbed and the efficiency of the photo-effect is optimised by way of this. In contrast, an optimisation of a band width of realisable terahertz frequencies as well as an efficiency of the opto-electronic semiconductor chips with the conversion of light into terahertz radiation or with the coherent detection of terahertz radiation is at the forefront as an important aim. Thereby, one is to take more into account than the efficiency of the photoeffect, so that new optimisation guidelines result. The terahertz efficiency is thereby improved by way of the following measures: the photosensitive layers (active layers 12) which are used in the THz antennae are developed and used with as low as possible band edge energy (band gap), thus with an as large as possible band edge wavelength—preferably based on InGaAs above a InP substrate—and laser light is applied with photon energies far above the band edge energy, for excitation. Materials with an as large as possible band edge wavelength should therefore be excited with as short-waved as possible lasers.

The photo-sensitive layers are then designed as thinly as possible, which can improve the terahertz frequency characteristics. Simultaneously, the laser light however should be greatly absorbed for a high efficiency, which is rendered possible by the large wavelength difference and a high absorption coefficient. What is particularly important is the large band edge distance, in particular with thin layers in the nanometer range, e.g. in InGaAs/InAlAs multilayer photoconductors of the type shown in FIGS. 3 and 4, which can even be transparent due to the quantum well effect. The shortness of the wavelength of the laser light however must be limited such that no significant absorption occurs with the often advantageous embedding of the photosensitive layers between the boundary layers with a greater band distance, so that light losses at the wrong location are avoided.

The demand for fibre-connected systems is a reason for a further limitation of the laser wavelength. Either dispersion compensating fibres should be available or fibres with a negligible dispersion, for the laser wavelengths, so that the transmission of pulses here is possible without complicated additional measures such as open-beam grating arrangements. For this reason, wavelengths in the so-called O-band at 1310 nm are optimal, since here a zero-dispersion of the SSMF is present and an adequately large wavelength distance to the band edge wavelength of the preferred material InGaAs on InP is given and the normal border surfaces here can be designed in a transparent manner.

Figure 10:
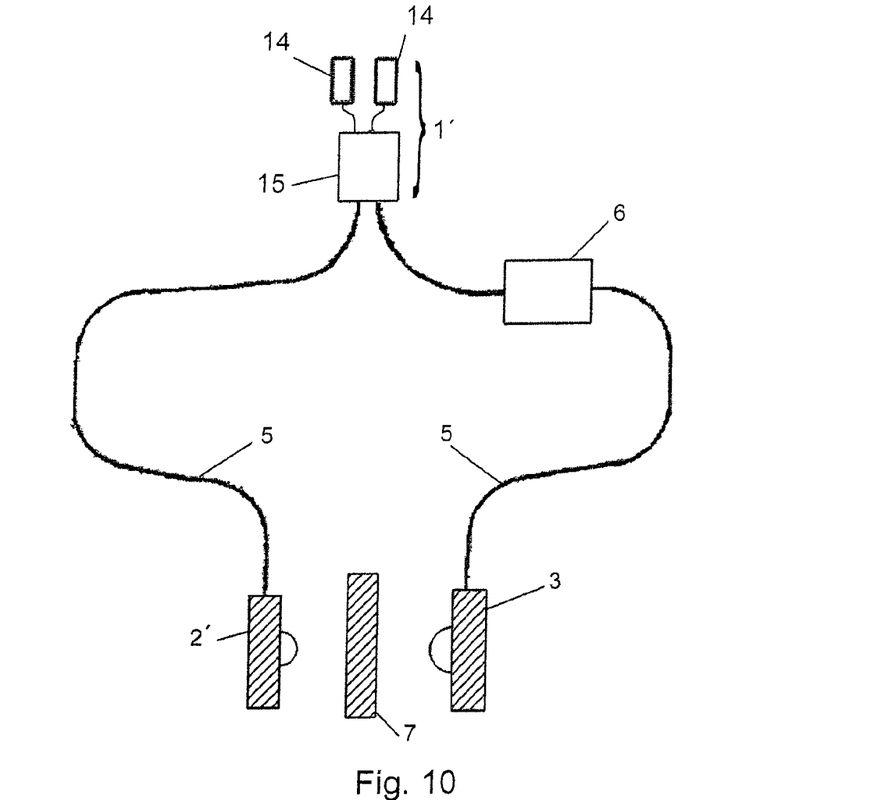

A further terahertz system which differs from the previously described terahertz system by a different laser light source 1' as well as a different transmitter antenna 2' is shown in FIG. 10. Recurring features here are again provided with the same reference numerals. In particular, the same receiver antenna 3 is used. Here, the laser light source 1' is given by a system with two individual lasers 14 of slightly different wavelengths and a coupler 15 with two inputs and two outputs for superimposing laser radiation of the two lasers 14 and for feeding a thus produced beat signal into the fibre-optics 5. The beat signal thereby has a beat frequency of about 1 THz, wherein this beat frequency can also be adjusted if the wavelength of at least one of the two lasers 14 can be controlled. A two-mode laser for producing the beat signal and for feeding this into the fibre optics 5 can also be used instead of the laser light source 1' constructed in such a manner.

Figure 11:
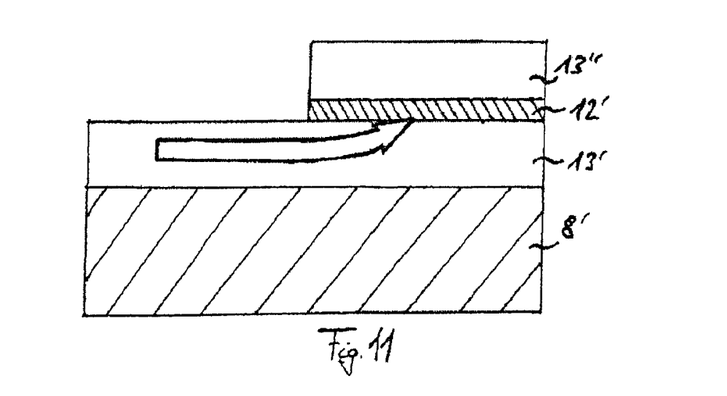

The transmitter antenna 2' here is also realised by an opto-electronic semiconductor chip, however, differing from the previously described embodiment example, is based on a photodiode, of which a cross section is shown in FIG. 11. Here too, a photosensitive, active layer 12' is arranged above a substrate 8' of the semiconductor chip which is formed from InP. The active layer 12' is formed from non-doped InGaAs and has a layer thickness of a little less than 100 nm. The active layer 12' thereby has a band edge wavelength of about 1650 nm, which is significantly greater than a wavelength of the laser light source 1' which is between 1260 nm and 1360 nm and is preferably adjustable in this region.

The active layer 12' is separated from the substrate 8' by a layer 13' which is adjacent thereto and which is formed from n-doped InGaAsP. A further layer 13" of p-doped InGaAsP adjacent thereon is arranged above the active layer 12'. Correspondingly doped InGaAlAs for the layers 13' and 13" could also be used instead of InGaAsP. The layers 13' and 13" are thereby designed such that a band edge wavelength of these layers 13' and 13" is about 1200 nm and is thus significantly smaller than the wavelength of the laser light source 1'.

The layers 13' and 13' which are adjacent the active layer 12' not only serve for realising a p-n transition of the photodiode and as their contact layers. Moreover, the layer 13' which is transparent to the light of the laser light source 1' serves as a waveguide layer, into which the light of the laser light source 1' is fed horizontally. This light is illustrated in FIG. 11 by an arrow. As can be well recognised in FIG. 11, the light of the laser light source 11' which is led through one of the two fibre optics 5 onto an end-face of the semiconductor chip of the transmitter antenna 2', propagates through the layer 13' and thus gets to the active layer 12' where it is absorbed and renders the photodiode biased in the blocking direction conductive. This, with the selected beat frequency of the laser light source 1', in turn leads to the production of terahertz radiation emitted from the transmitter antenna 2'.

Figure 12:
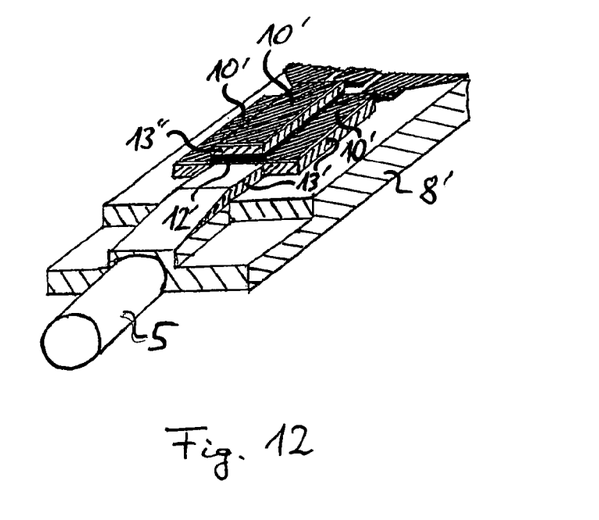

A detail of the transmitter antenna 2' together with one end of the fibre optic 5 is represented perspectively in FIG. 12. This detail in particular includes the described photodiode, wherein recurring features again are provided with the same reference numerals. The described components of the transmitter antenna 2' are thereby not represented true to scale. Electrical contacts 10' which are arranged on the layers 13' and 13" adjacent the active layer 12', are also recognisable here.

Figure 13:
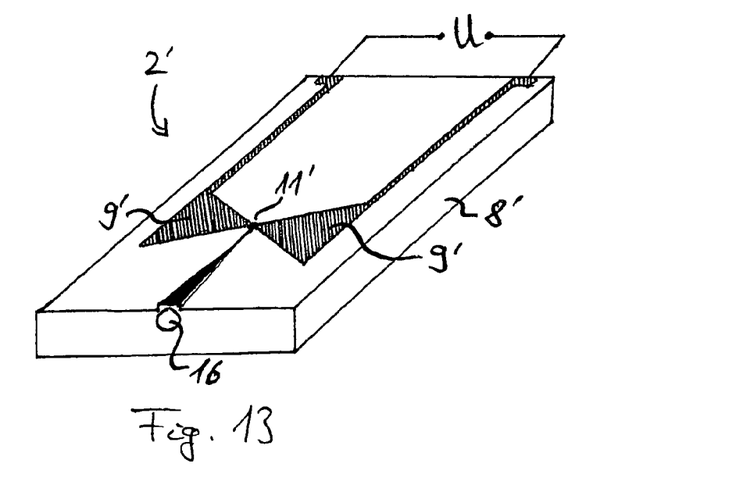

The semiconductor chip forming the transmitter antenna 2' is to be completely seen in FIG. 13. Here, one can also recognise two antenna conductors 9' which are arranged on the substrate 8' and are separated from this by a thin insulation layer. One of the antenna conductors 9' is connected to the n-doped layer 13', and the other antenna conductor 9' to the p-doped layer 13", via contacts 10'. The photodiode represented in FIGS. 11 and 12 and which is orders of magnitude smaller than the antenna conductors 9', is located between these antenna conductors 9' and forms a light-sensitive region 11' of the transmitter antenna 2'. A connection of the transmitter antenna 2' to a voltage source which is connected to the antenna 1 conductors 9' via two strip conductors and which is set under voltage by the photodiode is only represented schematically in FIG. 13. A coupling-in surface 16 which is optically coupled to the output of the fibre optic 5 is to be recognised on an end-face of the substrate 8'

The speed and frequency behaviour of photodiodes are essentially determined by the transit time of the produced photo charge carriers from the absorbing layer to the p-doped or n-doped boundary layers with a greater band distance. The transit time is usually improved by a voltage which is applied in the blocking direction. The transit time can technologically be further minimised by way of the reduction of the travel distance for the charge carriers, i.e. by way of thinner, absorbing layers. With this however, the light absorption and efficiency also greatly drop. A first measure to counter this is not to illuminate the layer perpendicularly, but laterally as described here. A longer design of the layers would increase the absorption, but would lead to an averaging via the light modulation, which would worsen the frequency behaviour. An improved measure here too is therefore the use of shorter wavelengths for exciting the active layer 12' which with shorter wavelengths has a higher absorption coefficient. The relations shown in FIGS. 6-9 thus also apply to the transmitter antenna 2'. The photosensitive layer 12' is embedded between a p-n transition from the layers 13' and 13" with a greater band distance, thus with a smaller band edge wavelength. Light absorption in these layers 13' and 13" would upset the function and efficiency of the photodiode and is therefore avoided by way of the wavelength of the laser light source 1' being selected larger than the band edge wavelength of the layers 13' and 13". A good compromise between the function and transparency of the adjacent layers 13 and 13" is achieved by band edge wavelengths of these boundary layers in the range of 1150 nm to 1200 nm. The transmitter antenna 2' can be operated efficiently given an activation in the O-band by way of this.

With the terahertz system shown in FIG. 10, it is the case of a fibre-coupled continuous wave terahertz system (CW system), with which the terahertz antennae are activated by laser light in the region of 1310 nm±50 nm and which thereby operates in an efficient manner. The light coupled into the fibre optics 5 from the lasers 14, of which at least one can be tuned in wavelength, is previously superimposed in the coupler 15 amid the same polarisation, in order to produce the beat signal. A time shift or phase shift between the two output signals which are used for activating the terahertz antennae, can be set and modulated in a controlled manner by way of the delay circuit 6 which can be given by a delay conductor or by a phase modulation device for one of the two wavelengths of the two lasers 14.

A fundamental insight for the realisation of the suggested terahertz systems is the fact that the significance of a trivially appearing parameter for optimising the chips was previously not recognised or even falsely interpreted. This parameter is the wavelength difference or energy difference between the exciting light and the band edge of the absorbing material. Here, until now, an as large as possible, but still absorbing wavelength of the light was seen as being advantageous, since with this, a given light power is converted into an as large as possible number of electron-hole pairs, i.e. the efficiency of the conversion of optical power into photo charge carriers is optimal. In contrast, with shorter wavelengths and higher photon energies, less charge carriers are produced and the excess energy leads to an additional heating which not without reason is seen as being unfavourable.

A completely different picture results if one places the optimisation of the photomixers, thus of the THz antennae as a whole, at the forefront. Hereinafter, it is specified as to why as thin as possible, absorbing layers are an important key parameter for optimising the speed of the photoconductors as well as of the photodiodes. The thin layers however must absorb the exciting light to an adequately great extent, otherwise the efficiency is lost. Thin layers (speed) and high light absorption (efficiency) can be realised simultaneously if one uses wavelengths which are as short-waved as possible, thus energetically lie as far as possible above the band edge. The band edge—perhaps differently than the name implies—is not a step function which jumps from transparency to a high, fixed absorption coefficient. Rather, a steep rise of the absorption coefficient begins in the band edge region and this rise continues far beyond the band edge region into the highly energetic, shorted-waved region. This can be well recognised in FIG. 6. One can therefore ascertain that the absorption coefficient becomes increasing larger with shorter and shorter wavelengths of the light, and a strong light absorption and thus a high efficiency can also be achieved with sub-μm thin layers which are optimised for high speed.

With the technological realisation of the components or the construction of the terahertz system, limitations can now however also occur, which set limits to an infinitely far shifting of the light wavelength. The optimal wavelength region is 1310 nm±50 nm in the so-called O-band of telecommunication, for the fibre-coupled pulsed system and CW system and when using photosensitive layers of InGaAs on InP.

Photoconductors for conventional fibre systems at 1550 nm are based on LT-InGaAs-nanolayers which are embedded between InAlAs layers with deep traps and are grown with an MBE on InP substrate. The required effect of the InAlAs boundary layers is more intense, the thinner the InGaAs photoconductor layer. The InGaAs is 12 nm thick in already established structures. In order with these thin layers, to achieve an adequately high absorption, the structures are periodically repeated, e.g. 100 times, so that a total thickness of the InGaAs of 1.2 μm results.

A further reduction of the InGaAs layer thickness would in principle lead to a further optimisation of the InAlAs effect and of the component characteristic. A reduction of the InGaAs thickness however leads to an ever increasing quantum well effect. This means that the sub-band energy level of the thin InGaAs of 1650 nm is shifted to approx 1600 nm by the quantum-well effect. With a further reduction of the layer thickness, the material is finally transparent to 1550 nm and the optimisation by thinner layers is therefore no longer possible with 1550 nm light. However, if one uses shorter wavelengths as is suggested here, then an optimisation of the InGaAs/InAlAs photoconductor is possible. Thus the band edge wavelength (e.g. 1550 nm) is still adequately distanced to the laser wavelength, even with thinner layers and a larger quantum well effect, so that a good absorption at 1310 nm is present (and certainly at even shorter wavelengths).

It is to be noted that shorter wavelengths and thin absorbing layers also make sense with conventional photoconductor layers without the quantum-well effect. The photo charge carriers are then produced superficially and the electrical fields act effectively by way of surface contacts. This is particularly advantageous with so-called finger contacts, with which the distance of the electrical contacts is only approx. 1 μm. The distance to the contacts is further for photo charge carriers which are not produced until at 1 or 2 μm depth, and the electrical fields act in a significantly reduced manner in the depth of the material. It can be shown that mesa-structuring and side contacts of the type shown in FIG. 3 may here effect a very significant and important improvement. This mesa-structuring however is technologically very complicated and is difficult to realise with the narrow finger contacts. The production of photo charge carriers close to the surface by way of short-waved excitation is therefore a meaningful measure for improving the function and effectiveness of the rapid photoconductors.

With multilayer structures there are limits to a meaningful, short-waved wavelength shifting, caused by the absorption of the surrounding layers which sets in. However, this would not be the case until wavelengths of less than 100 nm for InGaAs.

Fibre amplifiers based on praseodymium doping exist for the O-band. Mode-coupled semiconductor lasers are also conceivable as alternatives. Corresponding pulsed lasers with wavelengths of 1310 nm are possible, in particular based on InP.

Preferably photodiodes with integrated THz antennae as powerful transmitters are applied in fibre-based CW systems, whereas the photoconductors described above serve as coherent receivers.

As thin as possible absorbing layers for optimising the functional speed are to be strived for, also for photodiodes. The speed of photodiodes is limited by the transit time. This means that photo charge carriers are produced in an undoped absorber layer, which must then move to the p-doped or n-doped layer (having a greater band distance) which lie thereabove or therebelow. The thickness of the absorber layer is again an important optimisation criterion. However, it is the case that the absorption and the effectiveness reduce with thin layers. A first step for improvement is the lateral beaming into thin layers. The absorber layer is then typically integrated above the waveguide layer. The light from a glass fibre—supported by an integrated so-called taper—is beamed into the waveguide at the facing, and then after a certain path distance couples into the absorber layer lying thereabove. Adequate absorption can be achieved by way of greater lengths (7 μm to 20 μm) even with typical 0.3 μm thin absorber layers.

The terahertz application demands higher frequencies than telecommunication applications. Even thinner absorbing layers are therefore desirable. The length thereby cannot however be increased further, since the absorber length must be significantly shorter than the wavelength of the exciting, optical beat signal, in order to avoid a smoothing of the modulations.

Here too, one is to strive for as short as possible wavelengths of the optical control signal on the way to rapid photodiodes with thin, but effective absorber layers. Here too, the boundary layers of the absorber are limiting. The waveguides in the InP material system typically demand a band edge at 1150 nm to 1200 nm (or longer waved). Light of wavelengths below approx. 1250 nm is absorbed in the waveguide and thus does not reach the absorber, or only greatly weakened.

Thus a short-waved limit also applies to CW systems. Here too, the activation by beat signals with a centre of gravity in the O-band 1310 nm±50 nm is optimal, as well as the optimisation of the photodiode and photoconductors for this wavelength region amid the application of as thin as possible absorbing layers.

The invention claimed is:

1. A terahertz system for producing and coherently detecting terahertz (THz) radiation, the system comprising:
   a laser light source and at least two THz antennae that respectively via a fibre optic are optically coupled to the laser light source and are activatable by light of the laser light source, of which a first THz antenna serves as a transmitter antenna and a second THz antenna serves as a receiver antenna,
   wherein the THz antennae respectively comprise a semiconductor chip that is contacted by antennae conductors and comprises at least one active layer with a band edge wavelength that is larger than a wavelength of the laser light source, and at least one layer that is adjacent the active layer and that has a band edge wavelength that is smaller than the wavelength of the laser light source,
   wherein the at least one active layer of at least of one of the THz antennae is arranged between two of the adjacent layers and has a thickness that at the most corresponds to a penetration depth of the light of the laser light source, wherein the penetration depth is defined by an intensity drop to a share of 1/e of an incident radiation intensity, and wherein a semiconductor material forming the at least one active layer of at least one of the THz antennae has a band edge wavelength of at least 1600 nm, wherein the band edge wavelength at least of this at least one active layer of at least one of the THz antennae is at least 200 nm larger than the wavelength of the laser light source.

2. The terahertz system according to claim 1, wherein the band edge wavelength of the active layer of at least one of the THz antennae is at least 250 nm larger than the wavelength of the laser light source.

3. The terahertz system according to claim 1, wherein a semiconductor material forming the active layer of at least one of the THz antennae includes InGaAs.

4. The terahertz system according to claim 1, wherein at least one of the THz antennae is based on a photoconductor.

5. The terahertz system according to claim 1, wherein the transmitter antenna is based on a photodiode.

6. The terahertz system according to claim 1, wherein the at least one layer adjacent the active layer includes at least one of InGaAsP or InAlAs or InGaAlAs.

7. The terahertz system according to claim 1, wherein at least one of the adjacent layers of at least one of the THz antennae is configured as a waveguide, into which the light of the laser light source is coupled in a propagating manner in a plane defined by the at least one layer.

8. The terahertz system according to claim 1, wherein the wavelength of the laser light source lies between 1260 nm and 1360 nm.

9. The terahertz system according to claim 1, wherein the laser light source is given by a pulsed laser or by a two-mode laser or a system of two lasers for producing a beat signal of two laser waves of a beat frequency of 0.1 THz.

10. A terahertz system for producing and coherently detecting terahertz (THz) radiation, the system comprising:
 a laser light source, wherein the wavelength of the laser light source lies between 1260 nm and 1360 nm;
 a fiber optic coupler;
 first and second THz antennae, respectively optically coupled to the laser light source via the fiber optic coupler, the THz antenna being activatable by light of the laser light source, the first THz antenna configured as a transmitter antenna comprising a photodiode, and the second THz antenna configured as a receiver antenna, wherein at least one of the first and second THz antenna is based on a photoconductor;

wherein the THz antennae respectively comprise a semiconductor chip that is contacted by antennae conductors and comprises at least one active layer with a band edge wavelength that is larger than a wavelength of the laser light source, and at least one layer that is adjacent the active layer and that has a band edge wavelength that is smaller than the wavelength of the laser light source, wherein the active layer comprises at least one of InGaAs or InGaAsP or InAlAs or InGaAlAs;

wherein the at least one active layer of at least of one of the THz antennae is arranged between two of the adjacent layers and has a thickness that at the most corresponds to a penetration depth of the light of the laser light source, wherein the penetration depth is defined by an intensity drop to a share of 1/e of an incident radiation intensity, and wherein a semiconductor material forming the at least one active layer of at least one of the THz antennae has a band edge wavelength of at least 1600 nm, wherein the band edge wavelength at least of this at least one active layer of at least one of the THz antennae is at least 250 nm larger than the wavelength of the laser light source, wherein at least one of the adjacent layers of at least one of the THz antennae is configured as a waveguide into which the light of the laser source is coupled in a propagating manner in a plane defined by the at least one layer.

11. The terahertz system according to claim 10, wherein the laser light source is configured for producing a beat signal of two laser waves.

* * * * *